(12) United States Patent
Merilainen (10) Patent No.: US 9,557,298 B2
(45) Date of Patent: Jan. 31, 2017

(54) DEVICE FOR GENERATING MAGNETIC FIELD, METHOD FOR PREPARING SUCH DEVICE AND GAS SENSOR FOR MEASUREMENT OF PARAMAGNETIC GAS COMPONENT

(75) Inventor: Pekka Tuomo Merilainen, Helsinki (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 632 days.

(21) Appl. No.: 13/451,609

(22) Filed: Apr. 20, 2012

(65) Prior Publication Data
US 2012/0266656 A1 Oct. 25, 2012

(30) Foreign Application Priority Data

Apr. 21, 2011 (EP) ..................................... 11163327

(51) Int. Cl.
*G01N 27/74* (2006.01)
*H01F 41/00* (2006.01)
*H01F 17/06* (2006.01)

(52) U.S. Cl.
CPC ............... *G01N 27/74* (2013.01); *H01F 17/06* (2013.01); *H01F 41/00* (2013.01); *Y10T 29/49073* (2015.01)

(58) Field of Classification Search
CPC ..................... G01N 27/74; G01N 2291/02863; G01N 33/497; G01N 27/023; G01N 2011/147; Y10T 29/49073; H01F 17/06; H01F 41/00
USPC ............... 73/25.02, 31.05, 23.2, 24.01, 23.3, 24.06,73/1.06, 24.05, 64.53; 324/204, 201, 252, 228, 324/232, 244, 214, 262
See application file for complete search history.

(56) References Cited

U.S. PATENT DOCUMENTS

| | | | | |
|---|---|---|---|---|
| 3,049,665 A | * | 8/1962 | Hummel | ........................ 324/204 |
| 3,584,499 A | * | 6/1971 | Hummel | ...................... 73/25.02 |
| 3,866,461 A | * | 2/1975 | Machytka | .............. G01N 27/74 324/204 |
| 4,359,706 A | * | 11/1982 | Flack | ........................ H01F 7/00 335/281 |
| 4,464,926 A | * | 8/1984 | Albarda et al. | ................ 324/204 |
| 4,563,894 A | | 1/1986 | Karrer | |
| 4,633,705 A | * | 1/1987 | Merilainen et al. | .......... 73/31.04 |
| 4,667,157 A | * | 5/1987 | Ciammaichella | ....... G01N 27/74 324/202 |

(Continued)

FOREIGN PATENT DOCUMENTS

| | | |
|---|---|---|
| DE | 4201216 C1 | 2/1993 |
| EP | 1217369 A1 | 6/2002 |

(Continued)

OTHER PUBLICATIONS

European Search Report dated Feb. 29, 2012 for EP Application 11163327.7 filed on Apr. 21, 2011.

*Primary Examiner* — John Fitzgerald
*Assistant Examiner* — Marrit Eyassu
(74) *Attorney, Agent, or Firm* — GE Global Patent Operation; Marc A. Vivenzio (57) ABSTRACT

A device for generating a magnetic field, the device comprises a coil configured to respond to an electric current, a magnetic core comprising poles configured to generate a magnetic field close to the poles, wherein the magnetic field makes a paramagnetic gas component vibrate and emit an acoustic signal, wherein the magnetic core is surrounded at least partly by the coil, and a substrate at least partly covered by the magnetic core and the coil.

23 Claims, 4 Drawing Sheets

(56) References Cited

U.S. PATENT DOCUMENTS

| | | | |
|---|---|---|---|
| 4,672,346 A * | 6/1987 | Miyamoto | B29C 67/20 |
| | | | 335/296 |
| 4,818,966 A * | 4/1989 | Miyamoto | H01F 7/0278 |
| | | | 335/296 |
| 4,950,984 A * | 8/1990 | Otten et al. | 324/204 |
| 5,285,677 A | 2/1994 | Oehler | |
| 5,384,538 A * | 1/1995 | Ohta | G01R 33/3806 |
| | | | 324/318 |
| 5,539,366 A * | 7/1996 | Dorri | G01R 33/3806 |
| | | | 324/318 |
| 6,263,722 B1 * | 7/2001 | Fabinski | G01N 27/74 |
| | | | 324/201 |
| 2002/0062681 A1 * | 5/2002 | Livingston | 73/24.01 |
| 2007/0227230 A1 * | 10/2007 | Haveri et al. | 73/24.01 |
| 2008/0024118 A1 * | 1/2008 | Kahlman | G01N 27/745 |
| | | | 324/204 |
| 2010/0140519 A1 * | 6/2010 | Kopecek et al. | 251/129.15 |
| 2011/0057651 A1 * | 3/2011 | Duric | G01N 27/74 |
| | | | 324/252 |
| 2014/0113828 A1 * | 4/2014 | Gilbert et al. | 505/100 |

FOREIGN PATENT DOCUMENTS

| | | | | |
|---|---|---|---|---|
| EP | 1775582 A1 | 4/2007 | | |
| FI | EP 1217369 A1 * | 6/2002 | | G01N 21/41 |

* cited by examiner

DEVICE FOR GENERATING MAGNETIC FIELD, METHOD FOR PREPARING SUCH DEVICE AND GAS SENSOR FOR MEASUREMENT OF PARAMAGNETIC GAS COMPONENT

BACKGROUND OF THE INVENTION

Field of the Invention

Embodiments of the present invention relate generally to a device for generating magnetic field, a method for preparing a device for generating a magnetic field and a gas sensor for measurement of a paramagnetic gas component.

Description of the Prior Art

In anesthesia or in intensive care, the condition of a patient is often monitored, for example, by analyzing the gas exhaled by the patient for its content. For this reason, either a small portion of the respiratory gas is delivered to a gas analyzer or the gas analyzer is directly connected to the respiratory circuit. In the gas analyzer of mainstream type, the whole volume, or at least the main portion of the breathing air or gas mixture, flows through the analyzer and its measuring chamber. The mainstream sensors on the market have mostly measured only one gas, carbon dioxide.

Oxygen ($O_2$) is a gas most vital for life of all living subjects and in healthcare technology there is a firm need to continuously measure its concentration, especially under situations where patients breath artificial gas mixtures with $O_2$ concentrations higher than the 20.9% of the ambient air. This need is most obvious during anesthesia and intensive care. The measurement should be fast enough to be able to record oxygen values during both an inspiratory and an expiratory phase of the breathing cycle. To be able to cover an adequate range of breathing frequencies in children and adults, the response time should be 100 ms or better for both spontaneous and artificial mechanical ventilation. This response time guarantees that, in addition to recording inhaled $O_2$ level, one also gets accurate exhaled $O_2$ level to confirm oxygen delivery to the pulmonary blood. This also makes it possible to calculate $O_2$ uptake, if respiratory flow is also being measured. Traditional electro-chemical $O_2$ sensors have a response time of typically a few seconds. Even if they can be fabricated to achieve faster response times, it is on the cost of their life-time.

Oxygen differs physically from all other relevant respiratory gases appearing in a clinical environment by being strongly paramagnetic. This means that a force is acting on $O_2$ molecules in gradients of magnetic fields. Strictly speaking, this force is proportional to the product of the field strength and its spatial gradient. Generating an alternating field in a gas filled gap of an electro-magnet makes the oxygen molecules in the gap and close to its edges vibrate and generate a pressure signal in synchrony with the current applied to the coil of the magnet. The magnetic field strength is proportional to the flux density divided by the gap length and the pressure signal generated in an oscillating field proportional to the field squared. Even if this effect is macroscopically weak, it has been exploited commercially since the 1970-80's in both industrial and clinical gas measurement applications in various technical configurations.

The most widely used fast response differential paramagnetic $O_2$ analyzer in operation room and critical care application requires measuring in the side-stream set-up, which means the analyzer needs a gas sampling pump and a thin tubing to transport the gas from the patient airway to the measurement cell. This also generates a transport delay of typically 1 to 2 seconds between the signal measured and the real time concentration on the airway. The differential measurement based on this pneumatic bridge set-up also requires a reference gas to be suctioned into the sensor. In most cases, ambient air can be used as a valid reference gas.

There is also known a fast main-stream paramagnetic $O_2$ analyzer requiring no pumping of reference gas. This analyzer comprises an open solenoid type of an acoustic emitter claimed to emit sound with intensity proportional to $O_2$ concentration and a microphone for detection of an amplitude of the propagating sound generated. However, such a solenoid is a problematic component in this application because the dynamic magnetic forces acting on the coil generate an unwanted magneto-mechanical interference signal in phase with the net signal generated by $O_2$.

BRIEF SUMMARY OF THE INVENTION

According to an embodiment of the present invention, there is provided a device for generating a magnetic field. The device comprises a coil configured to respond to an electric current, a magnetic core comprising poles configured to generate a magnetic field close to the poles, wherein the magnetic field makes a paramagnetic gas component vibrate and emit an acoustic signal, wherein the magnetic core is surrounded at least partly by the coil, and a substrate at least partly covered by the magnetic core and the coil.

According to another embodiment of the present invention, there is provided a method for preparing a device for generating a magnetic field. The method comprises depositing a first coil layer on a substrate, depositing a magnetic core layer at least partly upon the first coil layer, depositing a second coil layer at least partly upon the magnetic core layer, and electrically connecting the first coil layer to the second coil layer.

According to another embodiment of the present invention, there is provided a gas sensor for measurement of a paramagnetic gas component. The gas sensor comprises a device for generating magnetic field comprising a coil configured to respond to an electric current, a magnetic core comprising poles configured to generate a magnetic field close to the poles, wherein the magnetic field makes a paramagnetic gas component vibrate and an emit acoustic signal, wherein the magnetic core is surrounded at least partly by the coil, and a substrate at least partly covered by said magnetic core and the coil, and an acoustic signal detector configured to receive the acoustic signal emitted by the paramagnetic gas component.

BRIEF DESCRIPTION OF THE DRAWINGS

Embodiments of the present invention will be more apparent to those skilled in the art upon reading the following description with reference to the accompanying drawings, in which.

DETAILED DESCRIPTION OF THE INVENTION

The above-mentioned shortcomings, disadvantages and problems in the prior art are addressed herein which will be understood by reading and understanding the following specification. Specific embodiments are explained in the following detailed description making a reference to accompanying drawings. These detailed embodiments can naturally be modified and should not limit the scope of the present invention as set forth in the claims.

Figure 1:
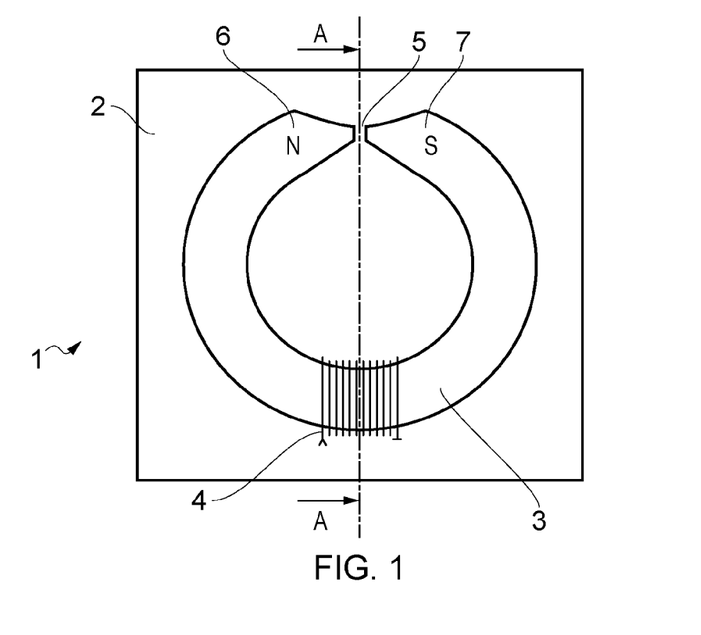
FIG. 1 is a schematic view of a device for generating magnetic field in accordance with an embodiment of the present invention.

In FIG. 1 a device 1 for generating a magnetic field is disclosed. The magnetic field in a gas space makes paramagnetic gas molecules vibrate and emit an acoustic signal, such as sound waves, that is useful while measuring a paramagnetic gas such as oxygen. The device 1 comprises a substrate 2, which can be made of a mechanically robust dielectric material such as a ceramic material or glass. The device 1 also comprises a magnetic core 3 typically made of a ferromagnetic material forming a circular electromagnet core layer and a coil 4 made of an electrically conductive material such as copper. The coil may be driven by AC or pulsating current. The magnetic core 3 surrounded at least partly by the coil 4 may be on a plane surface of the substrate 2. The coil 4 and the magnetic core 3 comprise thin integrated layers deposited on the substrate 2. The magnetic core 3 may also be planar lying on the plane surface of the substrate 2.

Figure 2:
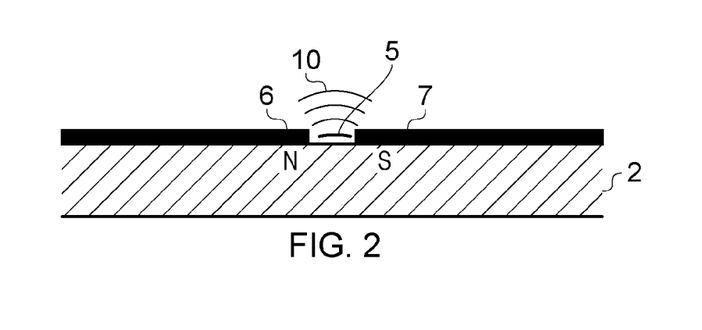
FIG. 2 is a side view of a device of FIG. 1 having an open gap between poles of a magnetic core in accordance with an embodiment of the present invention.
Figure 3:
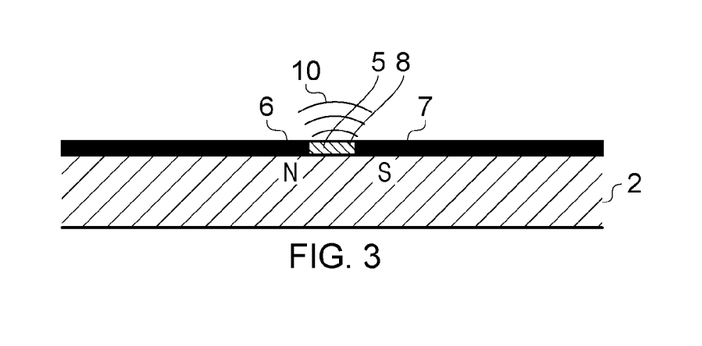
FIG. 3 is a side view of a device of FIG. 1 having a gap filled with dielectric material between poles of a magnetic core in accordance with an embodiment of the present invention.

The magnetic core 3, with poles 6 and 7, generates the magnetic field close to these poles, where the magnetic field is around or between the poles. An active acoustic waves emitting area 10 is created by a strong magnetic field in or around a gap 5 between the opposite poles 6 and 7 of the magnetic core 3 and its field gradients in proximity of its edges as shown in FIG. 2, where the gap 5 is open. One end of the gap 5, which is behind the gap 5, borders to the substrate 2, while its opposite end, which is away from the substrate 2, is in contact with ambient gas. The substrate 2 edging the gap 5 and opposite poles 6, 7, acts as a reflector of acoustic signals generated by vibrating paramagnetic gas molecules, which allows the gap 5 to emit sound in only one direction. This also means that by filling the gap 5 with a dielectric material 8, the area 10 immediately upon it will still act as the acoustic emitter in the presence of $O_2$ due to the fringe field and its gradient as shown in FIG. 3. Thus the $O_2$ molecules close to the gap 5 will still vibrate and emit acoustic waves. This filling will also contribute to minimizing the unwanted magneto-mechanical background signal. In the most basic version, a single short gap with the magnetic field acts as a line source of an acoustic wave with intensity proportional to ambient partial pressure of oxygen. The output for non-paramagnetic gases, like nitrogen, would be zero, assuming mechanical vibration of the gap 5 being negligible.

In the substrate 2 behind the gap 5 can also be an aperture (not shown) through the substrate 2 making possible also to generate the magnetic field, and thus emit acoustic signals, in opposite directions from the gap 5. One of the directions may be away from the substrate level as shown in FIG. 2, and another of the directions may be through the aperture of the substrate 2 to the other side. This naturally reduces the magnetic field and the acoustic emission away from the substrate 2, when the magnetic field and the emission is now divided into two opposite directions, but the acoustic emission can be increased, if necessary, by increasing the current supply to the coil. This kind of embodiment may be useful in applications like oxygen consumption measurement where both oxygen concentration and speed of gas could be measured concomitantly by utilizing the frequency difference between the two sound beams propagating in opposite directions (Doppler effect).

Figure 4:
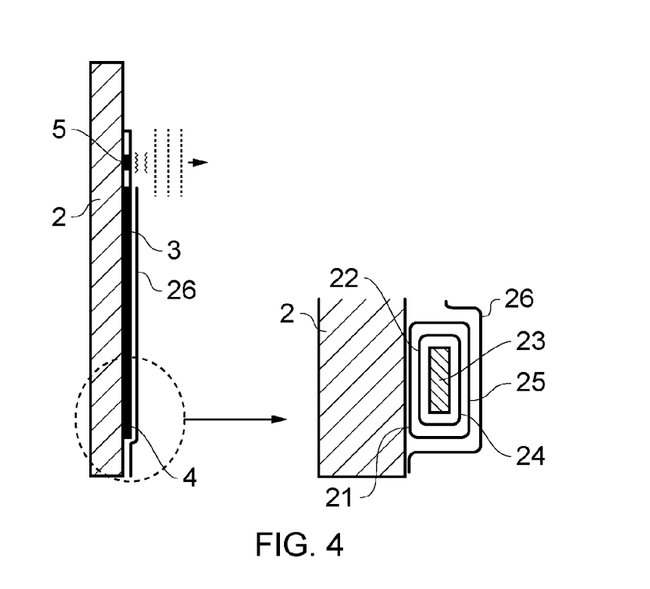
FIG. 4 is a cross section of the emitter device of FIG. 1 taken along lines A-A in accordance with an embodiment of the present invention.

FIG. 4 is a cross section of the emitter device 1 of FIG. 1 including an enlarged and more detailed view of the part where the magnetic core 3 is surrounded by the coil 4. The semi-planar coil 4 around the magnetic core 3 can be constructed by depositing a first coil layer 21, such as a bottom layer of a copper wire coil pattern, on the substrate 2. The first coil layer may then be covered by a first insulation layer 22 before depositing a magnetic core layer 23 of the magnetic core 3 as shown in the enlarged view of FIG. 4. When the magnetic core layer 23 is in place, at least those parts of the magnetic core layer may be covered by a second insulation layer 24, which may be in contact with a second coil layer 25 of the coil 4 which is deposited above the magnetic core layer 23 on the second insulation layer 24 so that the top pattern gets properly positioned as to the lower one to form a functional coil around the planar magnetic core as shown in FIG. 4. The thin insulation layers 22 and 24 are needed on both sides of the magnetic core layer 23 to prevent short circuit in the coil 4 if in contact with the magnetic core 3. Furthermore, the entire planar structure may be made inert by covering at least partly the magnetic core layer 23, or its top surface, and/or the second coil layer 25, by a dielectric layer 26 for protecting these components from corrosion and contamination. The top surface of the dielectric layer 26 is be provided away from the substrate. As shown in FIG. 1, to reduce the current needed to run the magnetic flux density up to saturation at lower currents, the width of the magnetic core 3 may be made to taper when nearing the gap 5, which can be open or closed.

Figure 5:
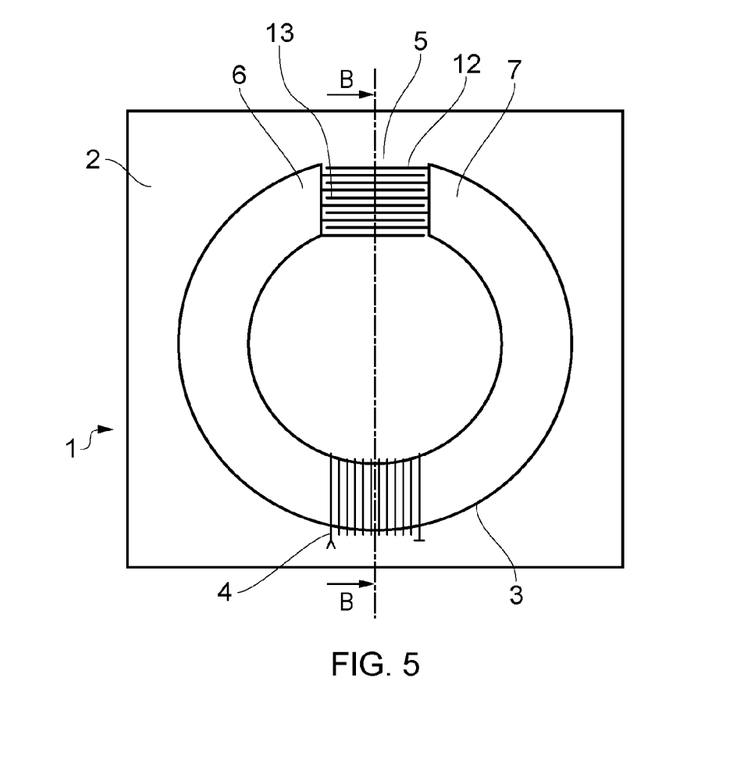
FIG. 5 is a schematic view of a device for generating magnetic field in accordance with an embodiment of the present invention.

Another embodiment of the device 1 is shown in FIG. 5. In the embodiment, the gap 5 is not tapered, but it is spread over a wider area to make the magnetic field and the acoustic wave emitting area extended to become like a 2-dimensional plane source. This can be made in various geometries by configuration where the gap 5 comprises interlaced protrusions 12 such as "fingers" with roots on the opposite poles 6 and 7 of the magnetic core 3. These protrusions 12 divide the gap 5 into several sub-gaps 13 enabling the wave front generated by a number of spatially distributed point sources to generate a more directional sound beam than the cylindrical or spherical one generated by a single gap 5 like in FIG. 1. Otherwise the structure of FIG. 5 is similar to the structure of FIG. 1.

Figure 6:
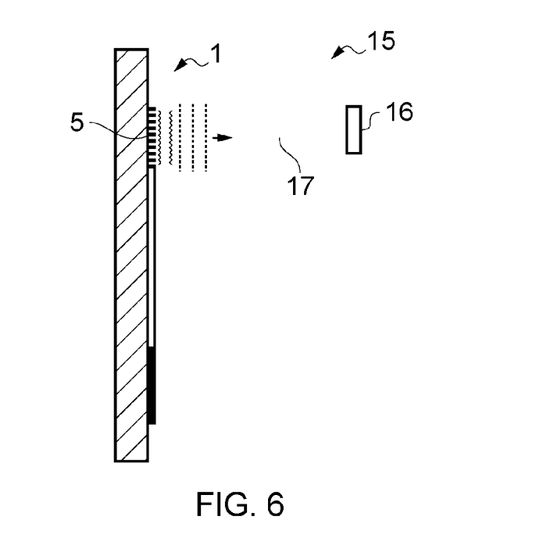
FIG. 6 is a schematic view of a cross section of a gas sensor comprising a device of FIG. 5 for generating magnetic field taken along lines B-B and a signal detector in accordance with an embodiment of the present invention.

The dimensions of the device 1 can be scaled according to the requirements of the application. Typically an area of the substrate 2 receiving the magnetic core 3, which can be used in a mainstream application to measure oxygen from breathing gases of a patient, especially adults, could be about 1 square inch and its thickness could be about 3 to about 5 mm. The thickness of the magnetic core layer 23 could be from about 0.2 to about 0.5 mm and the thickness of the coil conduits could be about 0.1 mm. The air gap of the magnetic core could be about 0.2 mm and the width of the magnetic core 3 could be about 5 mm with tapering down to about 1 mm if a point source as shown in FIG. 1 is required instead of a line source as shown in FIG. 6.

Figure 7:
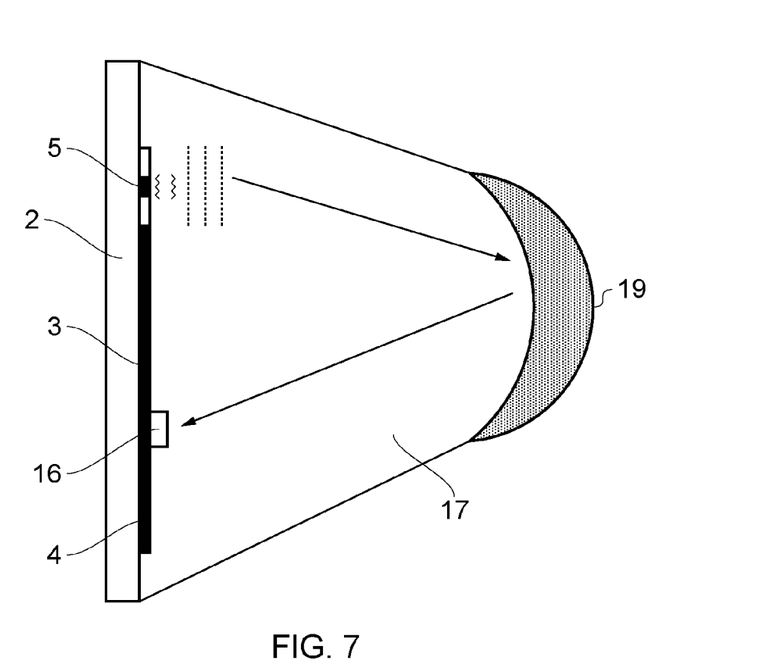
FIG. 7 is a schematic view of a cross section of a gas sensor comprising a device of FIG. 1 for generating magnetic field taken along lines A-A and a signal detector in accordance with an embodiment of the present invention.

In addition to the device 1 for generating the magnetic field, a gas sensor 15 for the paramagnetic gas may be provided. The gas sensor 15 may include an acoustic signal detector 16, such as a sound detector or microphone, to detect the acoustic wave to measure the amplitude of the acoustic wave as shown in FIGS. 6 and 7 and to provide a signal indicative of the concentration of the paramagnetic gas. There are two major options for their mutual positioning. As shown, in FIG. 6, the acoustic signal detector 16 may be positioned opposite to the device 1, leaving there between a gas space 17 with a gas mixture, which may include oxygen, which can be measured by the gas sensor 15. The acoustic wave propagates through the gas space 17 causing vibration of oxygen molecules in the gap 5, if not filled with the dielectric material, and around the gap 5 close to its edges. This in turn generates an acoustic signal, such as the sound wave, which can be detected by the acoustic signal detector 16. Another option for the gas sensor 15 is shown in FIG. 7 where both the device 1 and the sound detector 16 can be placed side by side, for instance, on the same substrate 2 or on the same wall. As shown in FIG. 7, a reflector 19, which can be the opposite wall itself or a separate structure close to the device 1, may also be provided. In this configuration, the acoustic wave propagates through the gas space 17 to the reflector 19, and the reflector 19 reflects the acoustic wave back across the gas space 17 to the acoustic signal detector 16. The reflector 19 can be designed to have a shape which ensures that reflected sound is focused optimally on the acoustic signal detector area. This integrated construction with the reflector 19 opens a convenient possibility to allow the sensor to measure ambient $O_2$ in any open space.

In accordance with another embodiment, the empty space on the surface of the substrate 2, inside or outside of the magnetic core 3, can be utilized for placement of extra sensors or sensor components, like ones for measuring the temperature and pressure (not shown) required for concentration versus partial pressure calculations, for instance, in a complete mainstream gas sensor. As explained above, the acoustic signal detector 16, or the pressure sensor to measure the amplitude of the sound signal generated by $O_2$ molecules, can be placed on the same substrate 2 with the magnetic core 3. Further, related to the possibility for simultaneous flow measurement in phase with the $O_2$ signal enabling real time $O_2$ consumption calculation, two sound detectors (not shown) can be placed on the substrate 2 in optimal positions to utilize Doppler shift to measure flows in both directions. Another option to the flow measurement is to place hot-wire flow sensor on the substrate (not shown).

Figure 8:
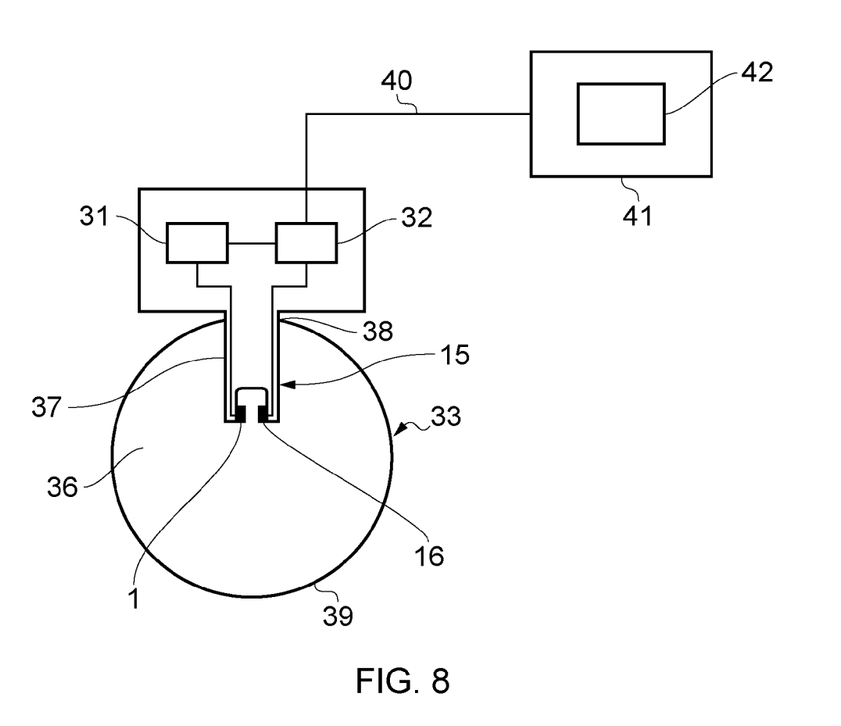
FIG. 8 is a schematic view of a gas sensor assembled into an airway adapter for analyzing a paramagnetic gas component in accordance with an embodiment of the present invention.

FIG. 8 shows a schematic view of a gas sensor 15 having both an emitter device 1 and an acoustic signal detector 16 assembled into an airway adapter 33. To analyze the paramagnetic gas, such as oxygen, the gas sensor 15 also comprises a current source 31 which generates current for the device 1 or for its coil 4. The gas sensor 15 further comprises a processing unit 32 for receiving a signal indicative of the concentration of the paramagnetic gas from the acoustic signal detector 16 and for receiving from the current source 31 a signal indicative of the pulsating current and its phase supplied to the coil 4. The processing unit may be further configured to control the operation of the current source 31. Based on the information collected from the current source 31 and the acoustic signal detector 16, the processing unit 32 is able to determine the paramagnetic gas concentration of the gas space 17 between the emitter device and the acoustic signal detector 16.

When measuring the patient gas, especially in neonatal and pediatric cases, it is crucial that the gas sensor 15 is fast, small and lightweight. Typically the patient is connected to a ventilator using an intubation tube, a Y-piece, an inspiratory limb and an expiratory limb (not shown), but the airway adapter 33 may be connected to the intubation tube. The gas sensor 15 is a so called mainstream gas sensor measuring gases flowing between the ventilator and the patient without drawing samples of the gas to a separate gas analyzer, such as a side stream gas analyzer, which is at a distance from the flow between the ventilator and the patient. Naturally, this same gas analyzer technology can also be exploited in side stream gas analyzers. The gas analyzer may also comprise other technology, such as infrared technology, when measurement of other gas such as carbon dioxide, nitrous oxide or any volatile anesthetic agents such as halothane, enflurane, isoflurane, desflurane and sevoflurane is required. Additionally, there may be a spirometry adapter (not shown) for measuring the gas flow in the respiratory circuit.

The gas to be measured in FIG. 8 flows through a gas channel 36 of the airway adapter 33. A cross section of the channel typically may be circular or square. The gas sensor 15 comprises a projective part 37, which can be pushed into the gas channel through an aperture 38 of the airway adapter 33. Both the device 1 and the acoustic signal detector 16 are fixed on the projective part 37. In one embodiment, the device 1 and the acoustic signal detector 16 are fixed on the tip of the projective part 37. The tip of the projective part 37 may be located at a distance from an edge 39 of the airway adapter 33 to avoid liquid drops moving along the edge 39 from disturbing the measurement. The gas sensor 15 shown in FIG. 8 is electrically connected via cable 40 to a patient monitor 41 having a display 42 for showing the measured oxygen concentration.

The adapter 33 may be made of a material allowing the acoustic signal generated by the device 1 to propagate through the material to the gas channel 36 inside the adapter 33 and finally to the acoustic signal detector 16, especially in embodiments where the device 1 for generating the magnetic field and the detector 16 are arranged outside the gas space of the adapter 33. Also, only a part of the airway adapter 33, which is critical regarding acoustic wave propagation, may be provided with a material allowing the acoustic signal generated by the device 1 to propagate through the material to the gas channel 36 inside the adapter 33 and to the acoustic signal detector 16.

In embodiments including infrared technology for measuring a substance other than the paramagnetic gas, the same airway adapter 33 may be equipped with a connection for the infrared technology (not shown). In such embodiments, the airway adapter 33 may be provided with at least one optical window for allowing the infrared radiation, which is used widely to analyze carbon dioxide, nitrous oxide and volatile anesthetic agents, to be absorbed due to the gas components. Typically, there are two infrared transmitting optical windows on the opposite sides of the gas channel 36. The infrared source may be located in the gas analyzer on one side of the adapter 33 and a non-dispersive filter assembly and an infrared detector or detectors on the opposite side in such a way that the infrared radiation is directed from the infrared source through the windows and respective narrowband filters to the infrared detector. The signal from the infrared detector may be amplified and modified to reflect the concentration of the gas to be measured.

In conclusion, compared to prior known devices for generating magnetic field the embodiments disclosed hereinbefore have several advantages. A robust integrated solid-state $O_2$ sensitive device for generating a magnetic field with minimal mechanical noise introduced will open an opportunity to construct a new generation, compact, fast response, mainstream $O_2$ gas sensor in a number of robust planar solid-state configurations. This device could also be utilized to construct a small stand-alone oxygen sensor for measurement of ambient oxygen partial pressure for personal safety in environments like, for example, high altitudes or underground mines.

The written description uses examples to disclose the present invention, including the best mode, and also to enable any person skilled in the art to make and use the present invention. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A device for generating a magnetic field comprising:
   a coil configured to respond to an electric current;
   a magnetic core comprising poles opposite each other separated by a gap, with protrusions rooted in each pole extending into the gap not connected with the opposite pole, said protrusions configured to generate a directional magnetic field close to the poles, wherein said directional magnetic field is configured so that induced oscillation of said field induces vibration of a paramagnetic gas in proximity to said field to generate a directional acoustic signal, the directional acoustic signal configured to be reflected by a reflector to a single-sided acoustic signal receiver.

2. The device for generating a magnetic field according to claim 1, wherein the coil comprises:
   a first coil layer deposited on the substrate; and
   a second coil layer deposited over the magnetic core and deposited at least partly over the first coil layer.

3. The device for generating a magnetic field according to claim 2, wherein the magnetic core comprises a magnetic core layer deposited at least partly over the first coil layer, wherein the second coil layer is deposited over the magnetic core layer and electrically connected to the first coil layer.

4. The device for generating a magnetic field according to claim 3 further comprising:
   a first insulation layer provided between the first coil layer and the magnetic core layer; and
   a second insulation layer provided between the magnetic core layer and the second coil layer.

5. The device for generating a magnetic field according to claim 1, wherein the substrate comprises a mechanically robust dielectric material.

6. The device for generating a magnetic field according to claim 1 further comprising a gap between the poles, wherein the gap is filled with a non-magnetic material.

7. The device for generating a magnetic field according to claim 1 further comprising a gap between the poles, wherein a width of the magnetic core tapers near the gap.

8. A method for preparing the device for generating a magnetic field according to claim 1, the method comprising:
   depositing a first coil layer on a substrate;
   depositing a magnetic core layer at least partly upon the first coil layer;
   depositing a second coil layer at least partly upon the magnetic core layer; and
   electrically connecting the first coil layer to the second coil layer.

9. The method for preparing a device for generating a magnetic field according to claim 8, further comprising:
   covering the first coil layer by a first insulation layer before depositing the magnetic core layer; and
   covering at least part of the magnetic core layer by a second insulation layer before depositing the second coil layer.

10. The method for preparing a device for generating a magnetic field according to claim 8, further comprising: covering the magnetic core layer at least partly by a dielectric layer.

11. The device for generating a magnetic field according to claim 1, wherein the acoustic signal is directed away from the substrate.

12. The device for generating a magnetic field according to claim 1, wherein the magnet core is planar, the substrate is planar, or the coil is semi-planar.

13. The device for generating a magnetic field according to claim 1, wherein the protrusions rooted in each pole are interlaced across the gap.

14. The device for generating a magnetic field according to claim 1, wherein additional sensors are integrated with the substrate in the same plane as the magnetic core.

15. The device for generating a magnetic field according to claim 14, wherein the additional sensors are at least one of: a pressure sensor, a temperature sensor, a current sensor, and a gas flow sensor.

16. The device for generating a magnetic field according to claim 1, wherein the protrusions are attached at the surface of each pole.

17. A gas sensor for measurement of a paramagnetic gas component comprising:
   a device for generating magnetic field comprising:
      a coil configured to respond to an electric current;
      a magnetic core comprising poles configured to generate a directional magnetic field close to the poles, wherein induced oscillations in the magnetic field induce a proximate paramagnetic gas to vibrate and generate a directed acoustic signal, wherein the magnetic core is surrounded at least partly by the coil; and a substrate having the magnetic core and the coil deposited upon it; and an acoustic signal detector configured to receive the directed acoustic signal formed by the vibrating paramagnetic gas component.

18. The gas sensor according to claim 17 further comprising:
   a current source configured to generate an electric current for the device and to provide a signal indicative of the electric current supplied; and
   a processing unit configured to receive a signal indicative of a concentration of the paramagnetic gas component from the acoustic signal detector, to receive from the current source a signal indicative of the current supplied to the coil, and, based on the information collected from the current source and the acoustic signal detector, to determine the paramagnetic gas concentration.

19. The gas sensor according to claim 18, wherein the processing unit is further configured to control the operation of the current source.

20. The gas sensor according to claim 17 further comprising a projective part in a gas channel.

21. The gas sensor according to claim 20, wherein both the device and the acoustic signal detector are fixed to the projective part, wherein the projective part is in contact with a gas flowing through the gas channel.

22. The gas sensor according to claim 17 further comprising a reflector positioned opposite the device, wherein the reflector is configured to reflect the acoustic signal towards the acoustic signal detector.

23. The gas sensor according to claim 22, wherein the acoustic signal detector and the device are fixed to a side of the substrate.

* * * * *